US006180802B1

(12) United States Patent
Chanteloup et al.

(10) Patent No.: US 6,180,802 B1
(45) Date of Patent: Jan. 30, 2001

(54) METHOD FOR SELECTIVE PROTECTION OF BACCATIN DERIVATIVES AND ITS APPLICATION TO TAXANE SYNTHESIS

(75) Inventors: Luc Chanteloup, Sargé-lès-le Mans; Bruno Chauveau, Le Mans; Christine Corbin, Etival - lès-le Mans; Robert Dhal, Le Mans; Sonia Le Guen, Reims; Arnaud Lamy, La Milesse; Antoine Leze; Jean-Pierre Robin, both of Le Mans, all of (FR)

(73) Assignee: Societe d'Etude et de Recherche en Ingenierie Pharmaceutique Seripharm, Le Mans (FR)

( * ) Notice: Under 35 U.S.C. 154(b), the term of this patent shall be extended for 0 days.

(21) Appl. No.: 09/077,099

(22) PCT Filed: Dec. 27, 1996

(86) PCT No.: PCT/FR96/02097

§ 371 Date: May 19, 1998

§ 102(e) Date: May 19, 1998

(87) PCT Pub. No.: WO97/24345

PCT Pub. Date: Jul. 10, 1997

(30) Foreign Application Priority Data

Dec. 27, 1995 (FR) .................................................. 95 15557

(51) Int. Cl.[7] ................................................... C07D 305/14
(52) U.S. Cl. ............................................ 549/510; 549/511
(58) Field of Search ...................................... 549/510, 511

(56) References Cited

U.S. PATENT DOCUMENTS 4,814,470 * 3/1989 Colin et al. ............................ 514/449
4,857,653   8/1989 Colin et al. ............................ 549/511

FOREIGN PATENT DOCUMENTS

WO95/020582   8/1995 (WO) .

OTHER PUBLICATIONS

International Search Report

* cited by examiner

*Primary Examiner*—Charanjit S. Aulakh
(74) *Attorney, Agent, or Firm*—Finnegan, Henderson, Farabow, Garrett, Dunner, L.L.P.

(57) ABSTRACT

New processes for the selective protection of the 7-position of 7,10-dihydroxytaxane derivatives, using β-substituted-alkoxycarbonyl groups which are more hindered than 2,2,2-trichloroethoxycarbonyl, and which are capable of being removed by a β-elimination mechanism, and the new intermediates resulting from these processes. The new intermediates of the invention are useful for preparing taxol and analogs thereof.

24 Claims, No Drawings

METHOD FOR SELECTIVE PROTECTION OF BACCATIN DERIVATIVES AND ITS APPLICATION TO TAXANE SYNTHESIS

This application is a 371 of PCT/FR96/02097 filed Dec. 27, 1996 now WO 97/24345 Jul. 10, 1997.

The present invention relates to new intermediates for the semisynthesis of taxanes and to the processes for preparing them.

Taxanes, natural substances whose diterpenic backbone is generally esterified with a β-amino acid side chain derived from N-alkyl- or N-aroyl-phenyl-isoserine, are known as anticancer agents. There are several tens of taxanes isolated from Taxaceae of the genus Taxus, such as for example, PACLITAXEL (R1=Ac, R2=Ph, R3=R4=H), cephalomanin, their derivatives which are deacetylated at the 10-position, or baccatins (derivatives without a side chain) represented by the formulae 1 and 2 below.

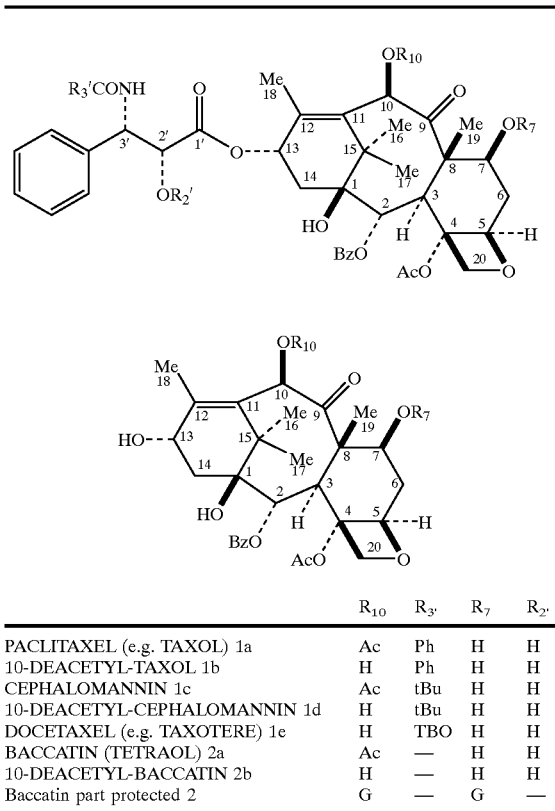

|  | $R_{10}$ | $R_{3'}$ | $R_7$ | $R_{2'}$ |
|---|---|---|---|---|
| PACLITAXEL (e.g. TAXOL) 1a | Ac | Ph | H | H |
| 10-DEACETYL-TAXOL 1b | H | Ph | H | H |
| CEPHALOMANNIN 1c | Ac | tBu | H | H |
| 10-DEACETYL-CEPHALOMANNIN 1d | H | tBu | H | H |
| DOCETAXEL (e.g. TAXOTERE) 1e | H | TBO | H | H |
| BACCATIN (TETRAOL) 2a | Ac | — | H | H |
| 10-DEACETYL-BACCATIN 2b | H | — | H | H |
| Baccatin part protected 2 | G | — | G | — |

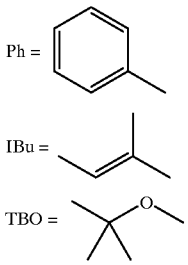

In an effort not to rapidly exhaust its original source, T. brevifolia, French researchers have sought to isolate PACLITAXEL from renewable parts (the leaves) of the European yew tree. They have thus identified the probable biogenetic precursor of taxanes, 10-deacetylbaccatin III, an ideal springboard for semisynthesis, because of its relative abundance in the leaf extracts.

The semisynthesis of taxanes, such as PACLITAXEL or DOCETAXEL (R1=AC, R2=t.butyloxy, R3=R4=H), therefore consists in esterifying the hydroxyl at the 13-position of a protected derivative of baccatin or of 10-deacetylbaccatin III with a β-amino acid derivative.

Various processes for the semisynthesis of PACLITAXEL or of DOCETAXEL are described in the state of the art EP-0,253,738, EP-0,336,840, EP-0,336,841, EP-0,495,718, WO 92/09589, WO 94/07877, WO 94/07878, WO 94/07879, WO 94/10169, WO 94/12482, EP-0,400,971, EP-0,428,376, WO 94/14787. Two recent manuals I. Georg, T. T. Chen, I Ojima, and D. M. Vyas, "Taxane Anticancer Agents, Basic Science and Current Status", ACS Symposium Series 583, Washington (1995) and in particular Matthew Suffness, "TAXOL® Science and Applications" CRC press, and 1500 cited references comprise exhaustive compilations of the semisyntheses of taxanes.

The selective monoprotection of taxanes dihydroxylated at the 7- and 10-positions has so far been obtained only with the aid of trialkylsilane ether groups (EP-A-0,336,840). This protection is of great interest because, on the one hand, of the rarity, for example, of baccatin III, direct precursor of PACLITAXEL and, on the other hand, of the impossibility of manufacturing it under profitable conditions from its much more easily available homologue, 10-deacetylbaccatin III, without an effective selective protection at the 10-position.

Indeed, the use of common groups such as acetate groups, or even of slightly hindered haloalkoxycarbonyls such as the conventional trichloroethoxycarbonyl to protect dihydroxytaxanes such as 10-deacetylbaccatin III, has the disadvantage of not at all being selective. On the other hand, they have up until now been widely used in the nonselective deprotection of 7,10-dihydroxytaxanes such as 10-deacetylbaccatin III, to give 7,10-di-(2,2,2-trichloroethoxycarbonyloxy)-10-deacetylbaccatin III, a key intermediate in the synthesis of DOCETAXEL (EP-A-0,336,841).

The use of trialkylsilanes for the protection of the hydroxyl situated at the 7-position of taxanes which are dihydroxylated at: the 7- and 10-positions has, because of the relative lability of these protecting groups towards slightly acidic media, a number of major disadvantages which counterbalance their good selectivity. The disadvantages are 1/ Subsequent acylation at the 10-position, which justifies prior selective protection at the 7-position, which is the case in the present invention, gives rise to 50 to 60% average yields because of the ease of trialkylsilylated ethers to be substituted by the acylating group present in the reaction medium, this situation being worsened by the greater difficulty of esterifying the 10-position when the 7-position is already occupied by a bulky group. This side reaction can be avoided provided it is carried out at a very low temperature using an alkali metal alcoholate as intermediate, but would introduce a new double disadvantage for an industrial synthesis as indicated in application WO-A-94/14787.

2/ The sensitivity of the alkylsilylated ethers to acidic conditions limits the possibilities of using acidic reagents in treatments of the subsequent synthetic sequence and therefore makes the field of application of these protecting groups a lot narrower. Furthermore, it should be noted that higher homologues such as tert-butyldimethylsilyl ether are thought to be more resistant to these conditions, but their introduction is made impossible because of their excessively large steric hindrance.

3/ The well-known sensitivity of alkylsilylated ethers to hydroxylated solvents such as water and alcohols makes the use of these solvents impossible in recrystallizations, systems which are nevertheless valuable because they are highly purifying in this series of compounds, which is another major disadvantage.

4/ The partial decomposition, during industrial chromatographic purifications of intermediates carrying silylated ethers, practically does not allow this purification technique to be used even though it is valuable for the purpose of producing high value-added pharmaceutical raw materials of high purity.

The taxoids not carrying a side chain of the following formula 3a:

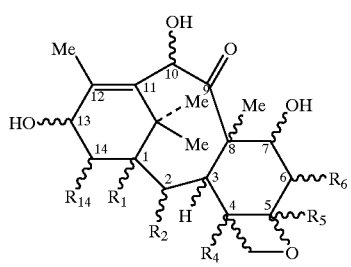

3a in which $R_1$, $R_2$, $R_4$, $R_5$, $R_6$, $R_{14}$ represent, independently of each other, a radical Q, with:

Q=R, H, OH, OR, SH, SR, OCOR, OCOOR, HCO, or X, and

X=halogen, and

R represents, a linear or branched alkyl, alkenyl, of alkynyl, alkenyl, or a alkynyl radical, a perhaloalkyl radical, a, heteroalkenyl, or heteroalkynyl linear or branched heteroalkyl radical, a cycloalkyl or cycloalkenyl radical, a heterocycloalkyl or heterocycloalkenyl radical, an aryl radical, an aralkyl radical, it being possible for the radicals to be substituted, in particular with one or more halogens or otherwise, their single multiple combined assemblies, and more generally any combination containing them in the form of single or repeated units, and in particular the derivatives of general formula 2 such as for example 10-deacetylbaccatin III often have at least four free hydroxyls, one which is tertiary, at the 1-position, highly hindered and only esterifiable under drastic conditions, the other three, which are secondary, at the 7-, 10- and 13-positions, easier to esterify, which can, on the basis of their steric hindrance, be divided into two reactivity groups:

the first, at the 13-position, is relatively hardly reactive to esterification under standard reaction conditions (including, according to the literature, for the introduction of the side chain);

the second group, at the 7- and 10-positions, which is of interest to the subject of the present invention, can, in turn, be divided into two levels, which are different in a subtle way, of reactivities towards esterification or carbonation, slightly in favour of the hydroxyl at the 7-position.

It also emerges from research that the two hydroxylation sites present a case of allosteric interaction: the introduction of a hindered ester into one of the 7- or 10-positions modifies the steric availability of the other position.

The present invention therefore relates to a new process for the selective protection at the 7-position of 7,10-dihydroxytaxanes of general formula 3a above, using particular reaction conditions, simultaneously with the use of alkoxycarbonyl groups substituted at the 2-(or β-) position which are more hindered than 2,2,2-trichloroethoxycarbonyl (which remains nonselective under our particular reaction conditions), which are capable of being removed by a β-elimination mechanism (*Protecting Groups*, P. J. Kocienski, Thieme Verlag Ed., p. 7 (1994) and cited references), and exhibiting none of the disadvantages of the trialkylsilylated ethers mentioned above.

Patent Application WO-A-94/07877 describes a process for the synthesis of taxanes, for which it is possible to use 2-trichloromethyl-2-propoxycarbonyl as protecting group for hydroxyls 7 and 10 of 10-deacetylbaccatin III. It emerges, however, from the description that this group is not used for the selective protection of the hydroxyl at the 7-position, but for the protection of the two hydroxyls 7 and 10, which is necessary for the preparation of DOCETAXEL, the only product really prepared in the examples, with moreover the only exemplified use of 2,2,2-trichloroethoxycarbonyl as protecting group. The teaching of this patent application therefore tends to lead persons skilled in the art away from the use of β-haloalkoxycarbonyl groups which are even more hindered than 2,2,2-trichloroethoxycarbonyl for the preparation of baccatin III protected at the 7-position, from 10-deacetylbaccatin III.

The invention also relates to the new intermediates resulting therefrom, the process for the selective acylation at the 10-position (in relation to the hydroxyl situated at the 13-position) of taxanes protected at the 7-position and the new 7-(β-substituted-alkoxycarbonyloxy)-10-acyloxytaxanes resulting therefrom, their use in coupling with side chains in taxanes and the new protected taxane intermediates resulting therefrom.

Finally, the present invention consists in describing the selective removal of the β-substituted-alkoxycarbonyl protecting groups leading to the final taxanes, in particular DOCETAXEL.

The present invention therefore relates, first of all, to a process for the preparation of 7-(β-substituted-alkoxycarbonyloxy)-10-hydroxytaxane derivatives corresponding to the following formula 3b:

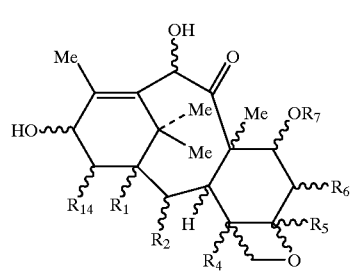

3b in which $R_1$, $R_2$, $R_4$, $R_5$, $R_6$, $R_{14}$ are defined above, $R_7$ represents an alkoxycarbonyl group substituted at the 2-(or β-) position which is more hindered than 2,2,2-trichloroethoxycarbonyl and which is capable of being removed by a β-elimination mechanism, by the slow addition, at a temperature greater than room temperature, contrary to the practice commonly used, preferably between 20 and 80° C., of the corresponding alkoxycarbonyl chloride substituted at the 2-position, diluted in an appropriate solvent, to a vigorously stirred solution of the 7–10-dihydroxytaxane of general formula 3a defined above in the presence of pyridine and/or of a hindered substituted pyridine, such as, for example, 4-pyrolidinopyridine or dimethylaminopyridine.

In particular, R7 represents an alkoxycarbonyl radical of general formula

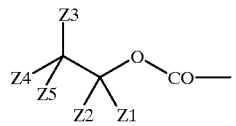

in which

Z1 and Z2 represent, independently of each other, a hydrogen atom, a radical R defined above or a halogen, Z3, Z4 and Z5 represent, independently of each other, a hydrogen atom, a halogen, a radical R, OR, $Si(R)_3$, R being defined above, or two of Z3, Z4 and Z5 together form part of a ring which is aromatic or otherwise, provided that when one of Z3, Z4 or Z5 represents a hydrogen atom, at least one of Z3, Z4 or Z5 represents a radical $Si(R)_3$, and provided that when one of Z3, Z4 or Z5 represents a halogen, Z3, Z4 and Z5 each represent a halogen chosen from bromine or iodine.

Advantageously, the esterification is carried out with 1 to 1.5 equivalents of chloroformate in relation to the 7–10-dihydroxytaxane of general formula 3a.

The 7-(β-substituted-alkoxycarbonyloxy)-10-acyloxytaxanes corresponding to the following general formula 3c:

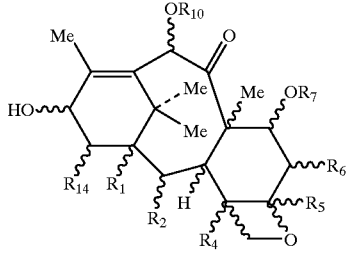

in which $R_1$, $R_2$, $R_4$, $R_5$, $R_6$, $R_7$ and $R_{14}$ are defined above, and $R_{10}$ represents an acyl radical of formula O—CO—R, R being defined above, are then prepared by the slow addition at room temperature of the corresponding acyl chloride (1 to 1.2 equivalents) diluted in an appropriate solvent to a vigorously stirred solution of the 7-(β-substituted-alkoxycarbonyloxy)-10-hydroxytaxane derivative obtained above, in the presence of pyridine and/or of a hindered substituted pyridine such as, for example, 4-pyrolidinopyridine or dimethylaminopyridine.

For these two reactions, the appropriate solvent is a nonhydroxylated solvent, in particular an alkyl halide such as, for example, methylene chloride, chloroform or dichloroethane.

The taxanes 3c protected at the 7-position which are obtained above, can be used for the semisynthesis of taxanes, by esterification of the hydroxyl at the 13-position with an appropriate taxane side chain precursor, in order to obtain a taxane derivative of general formula 3d

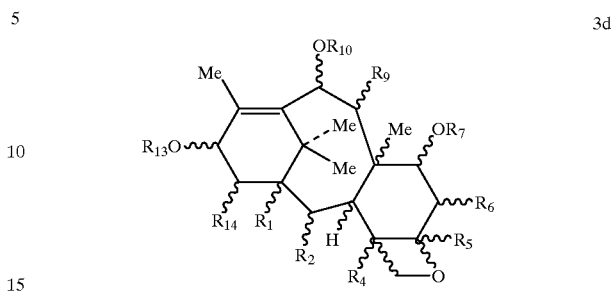

in which $R_1$, $R_{21}$, $R_4$, $R_5$, $R_6$, $R_7$, $R_{10}$ and $R_{14}$ are defined above, and $R_{13}$ represents a radical which is a taxane side chain precursor, and then by the selective deprotection of the hydroxyl at the 7-position, optionally accompanied and/or preceded by the opening and/or the conversion and/or the deprotection of the side chain precursor in order to obtain the desired taxane.

There will be used in particular the taxane side chain precursors described in the state of the art (EP-0,253,738, EP-0,336,840, EP-0,336,841, EP-0,495,718, WO 92/09589, WO 94/07877, WO 94/07878, WO 94/07879, WO 94/10169, WO 94/12482, EP-0,400,971, EP-0,428,376, WO 94/14787) or an oxazolidinone described in Patent Application FR-95 12 735, which is incorporated herein by way of reference. They may be in particular the following chain precursors:

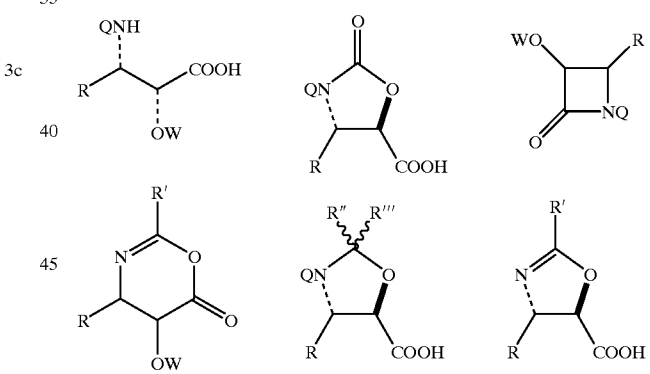

for which

Q=H, RCO, ROCO,

W=Bz or a group for protecting the hydroxyl functional group PG,

R'=R, OR, SR, X, Si(R)3,

R" and R'"=R.

R being defined above, combined with the derivative of formula 3c according to techniques known in the literature (EP-0,253,738, EP-0,336,840, EP-0,336,841, EP-0,495,718, WO 92/09589, WO 94/07877, WO 94/07878, WO 94/07879, WO 94/10169, WO 94/12482, EP-0,400,971, EP-0,428,376, WO 94/14787 or FR 95 12 735), in order to give the direct precursor of corresponding taxanes.

Advantageously, the following taxane side chain precursors will be used:

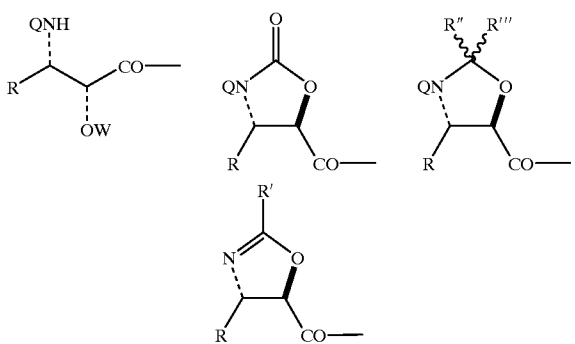

for which Q, R, R', R", R'" and W are defined above, in particular those for which R and R' represent an aryl, and Q represents an aroyl radical.

If an oxazolidinone described in Patent Application FR 95 12 735 is used, it will be preferably N-benzoyl-4-phenyloxazolidin-2-onecarboxylic acid, in particular the (4S, 5R) isomer, advantageously obtained by controlled saponification of the corresponding (+)-menthyl ester.

The deprotection of the hydroxyl at the 7-position of baccatin is carried out by β-elimination, according to the customary techniques [P. J. Kocienski, Protecting Groups, Thieme Verlag Ed., p. 7 (1994) and cited references].

Preferably, the group for protecting the hydroxyl functional group $R_7$ represents a radical of formula

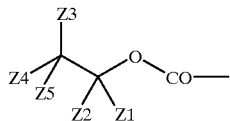

in which Z1 and Z2 represent a hydrogen atom.

When Z3, Z4 and Z5 represent a halogen, it is preferably a bromine.

According to another preferred embodiment of the invention, at least one of Z3, Z4 or Z5 represents an alkyl radical, and at least one of the remaining Z3, Z4 and Z5 represents a perhaloalkyl radical.

According to another preferred embodiment of the invention, two of Z3, Z4 and Z5 together form part of a fluorenyl ring.

Advantageously, the radical $R_7$ is chosen from the 2,2,2-tribromoethoxycarbonyl, 2-trichloromethyl-2-propoxycarbonyl, 2-trimethylsilylethoxycarbonyl and fluorenylmethoxycarbonyl groups.

The process according to the invention is described in a general way for 7,10-dihydroxytaxanes of general formula 3a since it relates to the selective protection of the hydroxyl at the 7-position, independently of the nature of the substituents $R_1$, $R_2$, $R_4$, $R_5$, $R_6$ or $R_{14}$. Of course, it is particularly appropriate for the protection of the 10-deacetylbaccatin of general formula 2 for which $R_7$ and $R_{10}$ represent a hydrogen atom, a key intermediate in the semisynthesis of PACLITAXEL.

The present invention therefore also relates to a process for the production of PACLITAXEL, obtained by esterification of the baccatin III derivative of general formula 2 for which $R_7$ represents a protecting group as defined above, and $R_{10}$ represents an acetyl radical, with an appropriate precursor of the side chain of PACLITAXEL, and then by deprotection of the hydroxyl at the 7-position according to the technique described above, optionally accompanied and/or preceded by the opening and/or the conversion and/or the deprotection of the PACLITAXEL side chain precursor, in order to give the said PACLITAXEL side chain.

Linear or branched alkyl is preferably understood to mean according to the invention a $C_1$–$C_6$ alkyl, in particular chosen from methyl, ethyl, propyl, isopropyl and butyl radicals and its various branched isomers such as, for example, tert-butyl, pentyl and hexyl and their various branched isomers. This definition also applies to the alkyl residues of the alkoxy, aralkyl or aralkoxy radicals.

Cycloalkyl is preferably understood to mean according to the invention a $C_3$–$C_6$ cycloalkyl, in particular chosen from the cyclopropyl, cyclobutyl, cyclopentyl or cyclohexyl radicals.

Aryl is preferably understood to mean according to the invention an aromatic or heteroaromatic radical, in particular chosen from the phenyl, naphthyl, anthryl, phenanthryl, pyridyl and pyrimidyl radicals, and the like.

Finally, halogen is preferably understood to mean chlorine, bromine or iodine. For the perhaloalkyl radicals, there will preferably be perchlorinated radicals, in particular the trichloromethyl or pentachloroethyl radicals.

Other characteristics of the processes and intermediates according to the invention will emerge in the light of the examples below.

Comparative Studies With the Aid of Haloalkoxycarbonyls

The principal object of this invention being to demonstrate the determining advantage, in terms of selectivity, of β-substituted alkoxycarbonyl protecting groups, which are more hindered than 2,2,2-trichloroethoxycarbonyl (Troc), already used nonselectively in the nonselective protection of taxanes having at least two free hydroxyls at the 7- and 10-positions (EP-A-0,336,841), the comparative kinetic study was carried out in relation to it.

By way of comparison, and without limiting the scope of the present invention, we selected as example 2,2,2-trichloro-tert-butoxycarbonyl (TCBoc) and tribromoethoxycarbonyl (Tbroc), protecting groups which are substantially more hindered than Troc, using as example of substrate 10-deacetylbaccatin III, the usual precursor for the semisynthesis of PACLITAXEL and of DOCETAXEL.

The reaction conditions used in this example of kinetic study are the following:

Temperature: 38° C.
Solvent: dichloromethane
Chloroformate: 1.1 to 1.5 molar equivalents
Total duration of the study: 16 hours
Catalysts: pyridine, 5 molar equivalents, 4-pyrolidinopyridine, 1.4 molar equivalents
Procedures: vigorous stirring, slow addition of chloroformate (1 molar equivalent per hour).

Quantitative analytical monitoring was carried out by high-performance liquid chromatography.

The results of this comparative kinetic study are collated in Table I below.

TABLE I

COMPARATIVE EXAMPLES OF PROTECTION OF
10-DEACETYLBACCATIN III: COMPARATIVE TABLE

| | Cumulative yield % |
|---|---|
| Protection by Troc, under the usual conditions | |
| 7-TROC-10-DAB III (0–25° C., DMAP, pyridine) | 49–54 |
| 7-TROC-BACCATIN III | 47–52 |
| Example of protection by Troc, under special conditions | |
| 7-TROC-10-DAB III (0–25° C., DMAP, pyridine) | 56–60 |
| 7-TROC-BACCATIN III | 51–57 |
| Example of protection by TCboc, under special conditions | |
| 7-TCBOC-10-DAB III (40-60° C., PP, pyridine) | 78–89 |
| 7-TCBOC-BACCATIN III | 75–87 |
| Protection by TES (comparative) | |
| 7-TES-10-DAB III* | 90–94 |
| 7-TES-BACCATIN III | 57–64 |

Abbreviations: TROC = 2,2,2-Trichloroethoxycarbonyl; TCBOC = 2,2,2-Trichloroterbutoxycarbonyl; TES = Triethylsilyl; DMAP = Dimethylaminopyridine; PP = 4-pyrolidinopyridine; DAB = deacetylbaccatin
*84–86% according to the literature [J. -N. Denis, A. Greene, J. Am. Chem. Soc., 5917 (1988)].

The results of this comparative study show without ambiguity that the new protecting groups according to the invention which are used for the synthesis of baccatin III protected at the 7-position make it possible to obtain 10-deacetylbaccatin III protected at the 7-position with a selectivity close to that of triethylsilyl, the only group used in the state of the art.

When the selective acylation of the hydroxyl at the 10-position is then carried out, yields are then obtained which are greater than those obtained with 7-triethylsilyl-10-deacetylbaccatin III.

An overall yield of synthesis of baccatin III protected at the 7-position from 10-deacetylbaccatin is therefore obtained which is greater than that obtained for the state of the art process (75–87% against 57–64%).

EXPERIMENTAL PART

EXAMPLE 1

7-O-(2,2,2-Trichloro-t-butoxycarbonyl)-10-deacetylbaccatin III

A solution of 0.26 g (1.10 mmol) of 2,2,2-trichloro-t-butoxycarbonyl chloride in 2 ml of dichloromethane is added, over 50 min, to a stirred solution, at 40° C. under an inert atmosphere, of 500 mg (0.919 mmol) of 10-deacetylbaccatin III and 0.19 g (1.29 mmol) of 4-pyrolidinopyridine in 5 ml of dry dichloromethane. After an additional 1 h of reaction, and returning to room temperature, the organic solution is washed with a 2% aqueous solution of HCl (5 ml), washed with osmosed water (2×5 ml), dried over MgSO$_4$ and concentrated under reduced pressure. After chromatography of the crude product on silica gel (15–40 µm) (eluent: cyclohexane-ethyl acetate, 60/40), 7-O-(2,2,2-trichloro-t-butoxycarbonyl)-10-deacetylbaccatin III is obtained in the form of a white powder (Y=89%).

The product obtained has the following characteristics:
$^1$H NMR 400 MHz (CDCl$_3$) (δ ppm): 8.10 (2H, d, J=7.3 Hz); 7.62 (1H, t, J=7.3 Hz); 7.49 (2H, t, J=7.6 Hz); 5.64 (1H, d, J=6.8 Hz); 5.50 (1H, d); 5.39 (1H, dd, J=10.6 and 7.3 Hz); 4.97 (1H, d, J=8.6 Hz); 4.89 (1H, m); 4.34 and 4.20 (2H, 2d, J=8.4 Hz); 4.09 (1H, d); 4.06(1H, d); 2.60 (1H, m); 2.31 (3H, s); 2.29 (1H, m); 2.13 (3H, s) and (1H, m); 2.06 (1H, m); 1.90 (6H, s); 1.85 (3H, s); 1.09 (3H, s); 1.06 (3H, s).

EXAMPLE 2

7-O-(2,2,2-Trichloro-t-butoxycarbonyl)-baccatin III

50 µl (0.695 mmol) of acetyl chloride are added to a stirred solution, at room temperature under an inert atmosphere, of 260 mg (0.347 mmol) of 7-O-(2,2,2-trichloro-t-butoxycarbonyl)-10-deacetylbaccatin III and 127.5 mg (1.04 mmol) of 4-dimethylaminopyridine in 2.5 ml of dry dichloromethane. After 1 h of reaction at room temperature, the organic phase is washed with a 2% aqueous solution of HCl until pH=6 is obtained, dried over MgSO$_4$ and concentrated under reduced pressure. After chromatography of the residue obtained on silica gel (15–40 µm) (eluent: cyclohexane-ethyl acetate, 6/4), 7-O-(2,2,2-trichloro-t-butoxycarbonyl)baccatin III is obtained in the solid state (Y=96%).

The compound obtained has the following characteristics:
$^1$H NMR 400 MHz (CDCl$_3$) (δ ppm): 8.10 (2H, d, J=7.6 Hz); 7.61 (1H, t, J 7.4 Hz); 7.48 (2H, t, J=7.7 Hz); 6.52 (1H, s); 5.65 (1H, d, J=6.9 Hz); 5.39 (1H, dd, J=10.4 and 7.3 Hz); 4.96 (1H, d, J=8.9 Hz); 4.86 (1H, m); 4.32 and 4.17 (2H, 2d, J=8.4 Hz); 4.01 (1H, d, J=6.9 Hz); 2.69 (1H, m); 2.30 (2H, m); 2.29 (3H, s); 2.16 (3H, s); 2.14 (3H, s); 2.07 (1H, d, J=4.8); 1.97 (1H, m); 1.95 and 1.91 (6H, 2s); 1.80 (3H, s); 1.61 (1H, s); 1.15 (3H, s); 1.07 (3H, s).

EXAMPLE 3 (COMPARATIVE)

7-O-trichloroethoxycarbonyl-10-deacetylbaccatin III

A solution of 0.152 ml (1.10 mmol) of trichloroethoxycarbonyl chloride in 2 ml of dichloromethane is added, over 40 min, to a stirred solution, at 40° C. under an inert atmosphere, of 500 mg (0.919 mmol) of 10-deacetylbaccatin III and 0.19 g (1.29 mmol) of 4-pyrolidinopryidine in 5 ml of dry dichloromethane. After an additional 1 h of reaction and returning to room temperature, the organic solution is washed with a 2% aqueous solution of HCl (5 ml), washed with osmosed water (2×5 ml), dried over MgSO$_4$ and concentrated under reduced pressure (HPLC yield=57%). After chromatography of the crude product on silica gel (15–40 µm) (eluent: cyclohexane-ethyl acetate, 60/40), 7-O-trichloroethoxycarbonyl-10-deacetylbaccatin III is obtained in the form of a white powder.

The product obtained has the following characteristics:
$^1$H NMR 400 MHz (CDCl$_{13}$) (δ ppm): 8.10 (2H, d, J=7 Hz); 7.62 (1H, t, J=7.4 Hz); 7.49 (2H, t, J=7.6 Hz); 5.65 (1H, d, J=6.9 Hz); 5.44 (1H, dd, J=10.8 and 7.3 Hz); 5.39 (1H, d); 4.98 (1H, d, J=7.5 Hz); 4.89 (1H, m); 4.84 and 4.70 (2H, 2d, J=11.9 Hz); 4.35 and 4.20 (2H, 2d, J=8.4 Hz); 4.10 (1H, d, J=7 Hz); 4.01 (1H, d, J=1.8 Hz); 2.64 (1H, m); 2.31 (3H, s); 2.29 (1H, m); 2.11 (3H, d); 2.05 (2H, m); 1.89 (3H, s); 1.09 (3H, s); 1.07 (3H, s)

EXAMPLE 4

7-O-trichloroethoxycarbonylbaccatin III
(comparative)

0.68 ml (0.695 mmol) of acetyl chloride is added to a stirred solution, at room temperature under an inert atmosphere, of 1.70 g (2.36 mmol) of 7-O- trichloroethoxycarbonyl-10-deacetylbaccatin III and 0.96 ml (12 mmol) of pyridine in 17 ml of dry dichloromethane. After 3 h of reaction at room temperature, the organic phase is washed with water (2×20 ml), dried over $MgSO_4$ and concentrated under reduced pressure. After chromatography of the residue obtained on silica gel (15–40 μm) (eluent: cyclohexaneethyl acetate, 6/4), 1.38 g of 7-O-trichloroethoxycarbonylbaccatin III are obtained in the solid state (Y=75%).

The compound obtained has the following characteristics:
$^1$H NMR 400 MHz ($CDCl_{13}$) (δ ppm): 8.11 (2H, d, J=7.1 Hz); 7.62 (1H, t, J=7.4 Hz); 7.49 (2H, t, J=7.6 Hz); 6.39 (1H, s); 5.64 (1H, d, J=6.9 Hz); 5.61 (1H, dd, J=10.7 and 7.2 Hz); 5.04 and 4.65 (2H, 2d, J=12 Hz); 4.99 (1H, d, J=8.2 Hz); 4.87 (1H, m); 4.33 and 4.16 (2H, 2d, J=8.4 Hz); 4.02 (1H, d, J 6.9 Hz); 2.64 (1H, ddd, J=14.4, 9.5 and 7.2 Hz); 2.30 (3H, s) and (2H, m); 2.17 (3H, s); 2.13 (3H, d, J=0.8 Hz); 2.04 (1H, m); 1.83 (3H, s); 1.63 (1H, s); 1.14 (3H, s); 1.09 (3H, s)

EXAMPLE 5

13-O-[[(4S,5R)-2,4-Diphenyl-4,5-dihydrooxazol-5yl]carbonyl]-7-O-(2,2,2-trichloro-t-butoxycarbonyl) baccatin III 2.61 g (12.7 mmol) of dicylcohexylcarbodiimide are added to a stirred solution, at room temperature and under an inert atmosphere, of 3.38 g (12.7 mmol) of (4S,5R)-2,4-diphenyl-4,5-dihydrooxazol-5-carboxylic acid in 60 ml of anhydrous toluene. After stirring for 5 min, 5 g (6.33 mmol) of 7-O-(2,2,2-trichloro-t-butoxycarbonyl)baccatin III and 0.77 g (6.33 mmol) of 4-dimethylaminopyridine are added, and the mixture is stirred at room temperature for 15 min. After removing the insoluble matter by filtration, the organic phase is concentrated under reduced pressure and the residue obtained is purified by chromatography on silica gel (15–40 μm) (eluent: cyclohexane-ethyl acetate, 9/1).

6.2 g of the compound cited in the title are thus obtained in the form of a white solid (Y=94%), which compound has the following characteristics:
$^1$H NMR 400 MHz ($CDCl_3$) (δ ppm): 8.18 (2H, d, J=7.2 Hz); 8.07 (2H, d, J=7.6 Hz); 7.64 (1H, t, J=7.4 Hz); 7.60 (1H, t, J=7.3 Hz); 7.52 (4H, m); 7.39 (5H, m); 6.47 (1H, s); 6.24 (1H, t, J=8.4 Hz); 5.70 (1H, d, J=7 Hz); 5.59 (1H, d, J=7.3 Hz); 5.35 (1H, dd, J=10.4 and 7.2); 4.93 (2H, d, J=7.3 Hz); 4.29 and 4.17 (2H, 2d, J=8.5 Hz); 3.96 (1H, d, J=6.9 Hz); 2.71 (1H, m); 2.37 (1H, dd, J=15.1 and 9.2 Hz); 2.28 (1H, dd, J=15.1 and 8.8 Hz); 2.13 (3H, s); 2.01 (6H, s); 1.95 and 1.93 (6H, 2s); 1.80 (3H, s); 1.72 (1H, s); 1.23 (3H, s); 1.18 (3H, s).

EXAMPLE 6

13-O-[(2R,3S)-O-Benzoyl-3-phenylisoserin-1-yl]-7-O-(2,2,2-trichloro-t-butoxycarbonyl)-baccatin III 0.2 ml (0.2 mmol) of a 1 M aqueous solution of HCl is added to a stirred solution, at room temperature and under an inert atmosphere, of 100 mg (0.0963 mmol) of 13-O-[[(4S,5R)-2,4-diphenyl-4,5-dihydrooxazol-5-yl]carbonyl]-7-O-(2,2,2-trichloro-t-butoxycarbonyl)baccatin III in a mixture of tetrahydrofuran (1 ml) and methanol (1 ml), and the reaction mixture is stirred at room temperature for 14 h 30 min. After addition of 15 mg (0.2 mmol) of solid sodium hydrogen carbonate followed by stirring for 10 min, the reaction medium is extracted with ethyl acetate (2×2 ml), and the organic phase is washed with water, dried over $MgSO_4$ and concentrated under reduced pressure.

102 mg of the compound cited in the title are thus isolated (crude yield=quantitative), which compound will be used as it is in the next step, and which has the following characteristics:
$^1$H NMR 400 MHz (DMSO-$d_6$) (δ ppm): 8.15 (2H, d, J=7.9 Hz); 7.97 (2H, d, J=7.7 Hz); 7.75 (2H, t, J=7.4 Hz); 7.64 (1H, t, J=7.7 Hz); 7.59 (1H, t, J=7.7 Hz); 7.48 (2H, d, J=7.3 Hz); 7.42 (2H, t, J=7.5 Hz); 7.42 (2H, t, J=7.5 Hz); 7.19 (1H, t, J=7 Hz); 6.34 (1H, s); 5.89 (1H, t, J=8.9 Hz); 5.47 (1H, d, J=7 Hz); 5.28 (1H, dd, J=10.5 and 7.3); 5.16 (1H, d, J=6.8 Hz); 4.98 (1H, d, J=9.5 Hz); 4.80 (1H, s); 4.41 (1H, d, J=6.8); 4.06 (2H, broad s); 3.72 (1H, d, J=7 Hz); 2.26 (3H, s); 2.07 (3H, s); 2.0 to 1.6 (4H, m); 1.86 (6H, s); 1.83 (3H, s); 1.64 (3H, s); 1.05 (3H, s); 1.01 (3H, s).

EXAMPLE 7

7-O-(2,2,2-trichloro-t-butoxycarbonyl)taxol 0.25 ml of a saturated aqueous solution of sodium hydrogen carbonate is added to a stirred solution, at room temperature and under an inert atmosphere, of 90 mg (0.0852 mmol) of 13-O-[(2R,3S)-O-Benzoyl-3-phenylisoserin-1-yl]-7-O-(2,2,2-trichloro-t-butoxycarbonyl)baccatin III in a mixture of tetrahydrofuran (4 ml) and methanol (4 ml), and the reaction mixture is stirred at room temperature for 48 h. After extraction of the reaction medium with ethyl acetate (2×5 ml), the organic phase separated is washed with water (5 ml), dried over $MgSO_4$, concentrated under reduced pressure and the residue obtained is purified by chromatography on silica gel (15–40 μm) (eluent: cyclohexane-ethyl acetate, 6/4).

63 mg of the product cited in the title are thus obtained in the form of a white solid (Y=70%), which compound has the following characteristics:
$^1$H NMR 400 MHz ($CDCl_3$) (δ ppm): 8.12 (2H, d, J=7.4 Hz); 7.75 (2H, d, J=7.3 Hz); 7.61 (1H, t, J=7.4 Hz); 7.50 (5H, m); 7.38 (5H, m); 7.19 (1H, d, J=9 Hz); 6.47 (1H, s); 6.18 (1H, t, J=8.6 Hz); 5.79 (1H, dd, J=8.9 and 2.2 Hz); 5.70 (1H, d, J=6.8 Hz); 5.33 (1H, dd, J=10.3 and 7.2); 4.93 (1H, d, J=9 Hz); 4.80 (1H, d, J=2.4 Hz); 4.31 and 4.21 (2H, 2d, J=8.5 Hz); 3.91 (1H, d, J=6.8 Hz); 2.66 (1H, m); 2.38 (3H, s); 2.33 (2H, m); 2.13 (3H, s); 1.99 (1H, m); 1.94 (3H, s); 1.90 (6H, s); 1.81 (3H, s); 1.19 (3H, s); 1.18 (3H, s).

EXAMPLE 8

13-O-[[(4S,5R)-2,4-Diphenyl-4,5-dihydrooxazol-5yl]carbonyl]baccatin III

300 μl (5.26 mmol) of acetic acid and 221 mg (3.38 mmol) of zinc powder are added to a stirred solution, at room temperature and under an inert atmosphere, of 390 mg (0.376 mmol) of 13-O-[[(4S,5R)-2,4-Diphenyl-4,5-dihydrooxazol-5-yl]carbonyl]-7-O-(2,2,2-trichloro-t-butoxycarbonylbaccatin III in 10 ml of ethyl acetate. After stirring for 1 h 15 min at 30° C. and checking by TLC, the organic phase after filtration is washed with osmosed water (5 ml), with a saturated aqueous solution of sodium hydrogen carbonate (2×5 ml), again with water (2×5 ml), dried over $MgSO_4$ and concentrated under reduced pressure.

314 mg of the compound cited in the title (crude yield=quantitative) are thus isolated, which compound will be used as it is in the next step and which has the following characteristics:
$^1$H NMR 400 MHz ($CDCl_{13}$) (δ ppm): 8.18 (2H, d, J=7.3 Hz); 8.07 (2H, d, J=7.4 Hz); 7.64 (1H, t, J=7.4 Hz); 7.60

(1H, t, J=7.3 Hz); 7.52 (2H, t, J=8.1 Hz); 7.50 (2H, t, J=7.8 Hz); 7.39 (5H, m); 6.27 (1H, s); 6.24 (1H, t, J=8.5 Hz); 5.67 (1H, d, J=7.1 Hz); 5.59 (1H, d, J=6.9 Hz); 4.96 (1H, d); 4.95 (1H, d, J=6.9 Hz); 4.29 and 4.15 (2H, 2d, J=8.4 Hz); 3.82 (1H, d, J=7 Hz); 2.57 (1H, ddd, J=15.9.6 and 6.8 Hz); 2.48 (1H, d, J=4 Hz); 2.38 (1H, dd, J=15.3 and 9 Hz); 2.27 (1H, dd, J=15.3 and 8.7 Hz); 2.24 (3H, s); 2.04 (3H, s); 1.89 (3H, s); 1.88 (1H, m); 1.75 (1H, s); 1.67 (3H, s); 1.26 (3H, s); 1.15 (3H, s).

EXAMPLE 9

Preparation of paclitaxel a) from 13-O-[[(4S,5R)-2,4-diphenyl-4,5-dihydro-oxazol-5-yl]carbonyl]-7-O-(2,2,2-trichloro-t-butoxycarbonyl) baccatin III 90 μl (0.09 mmol) of a 1 M aqueous solution of HCl are added to a stirred solution, at room temperature and under an inert atmosphere, of 15 mg (0.0148 mmol) of 13-O-[[(4S, 5R)-2,4-diphenyl-4,5-dihydrooxazol-5-yl]carbonyl]-7-O-(2,2,2-trichloro-t-butoxycarbonyl)baccatin III in a mixture of tetrahydrofuran (0.18 ml) and methanol (0.18 ml), and the reaction mixture is stirred at room temperature for 8 h. After addition of 0.6 ml of a saturated aqueous solution of sodium hydrogen carbonate, the solution is maintained homogeneous by addition of 1 ml of tetrahydrofuran and 1 ml of water, and the reaction medium is stirred for an additional 1 h 30 min. After addition of 2.5 ml of ethyl acetate and 2.5 ml of osmosed water, the residual aqueous phase is extracted with ethyl acetate (2.5 ml). The combined organic phases are dried over $MgSO_4$ and concentrated under reduced pressure.

14 mg of 7-O-(2,2,2-trichloro-t-butoxycarbonyl)taxol are thus obtained in the crude state (Y=93%) which are used without further purification in the next step.

30 μl (0.525 mmol) of acetic acid and 22.5 mg (0.344 mmol) of zinc powder are added to a stirred solution, at room temperature, of 13 mg (0.0128 mmol) of 7-O-(2,2,2-trichloro-t-butoxycarbonyl)taxol in 2 ml of ethyl acetate. After stirring for 2 h 30 min at room temperature and checking by TLC, and after dilution of the reaction medium with 3 ml of ethyl acetate, the organic phase is washed with osmosed water (1 ml), with a saturated aqueous solution of sodium hydrogen carbonate (1 ml), again with water, dried over $MgSO_4$ and concentrated under reduced pressure.

After chromatography of the crude product on silica gel (15–40 μm) (eluent: cyclohexane-ethyl acetate, 6/4), 9.5 mg of PACLITAXEL are thus isolated in the crystallized state (Y=89%).

b) from 13-O-[[(4S,5R)-2,4-diphenyl-4,5-dihydrooxazol-5-yl]carbonyl]baccatin III 0.7 ml (0.7 mmol) of a 1 M aqueous solution of HCl is added to a stirred solution, at room temperature and under an inert atmosphere, of 290 mg (0.347 mmol) of 13-O-[[(4S, 5R)-2,4-diphenyl-4,5-dihydrooxazol-5-yl]carbonyl] baccatin III in a mixture of tetrahydrofuran (4 ml) and methanol (4 ml), and the reaction mixture is stirred at room temperature for 4 h. After addition of 6 ml of a saturated aqueous solution of sodium hydrogen carbonate, the solution is maintained homogeneous by addition of 10 ml of water, and the reaction medium is stirred for an additional 3 h 30 min. After addition of 20 ml of ethyl acetate and 10 ml of osmosed water, the residual aqueous phase is extracted with ethyl acetate (20 ml). The combined organic phases are dried over $MgSO_4$ and concentrated under reduced pressure.

After chromatography of the crude product on silica gel (15–40 μm) (eluent: cyclohexane-ethyl acetate, 5/5), 270 mg of PACLITAXEL are thus isolated in the crystallized state (Y=93%).

What is claimed is:

1. A process for the preparation of a 7-(β-substituted-alkoxycarbonyloxy)-10-hydroxytaxane derivative corresponding to the formula 3b:

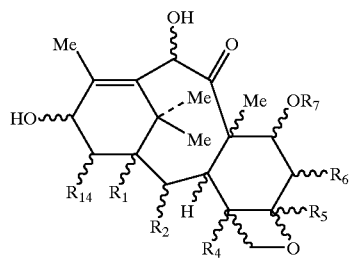

3b in which $R_1$, $R_2$, $R_4$, $R_5$, $R_6$ and $R_{14}$ are each the same or different and each represents a radical Q, wherein:

Q is H, OH, R, OR, SH, SR, OCOR, OCOOR, HCO or X, wherein

X is a halogen atom, and

R represents a linear or branched alkyl, alkenyl or alkynyl radical, a perhaloalkyl radical, a linear or branched heteroalkyl, heteroalkenyl or heteroalkynyl radical, a cycloalkyl or cycloalkenyl radical, a heterocycloalkyl or heterocycloalkenyl radical, an aryl radical or an aralkyl radical, wherein said radicals are unsubstituted or substituted; and $R_7$ represents an alkoxycarbonyl group substituted at the 2-position which is more hindered than 2,2,2-trichloroethoxycarbonyl and which is removable by a β-elimination mechanism, wherein said process comprises the slow addition, at a temperature greater than room temperature, of the alkoxycarbonyl chloride substituted at the 2-position corresponding to the alkoxycarbonyl group at $R_7$, diluted in an appropriate solvent, to a vigorously stirred solution of the 7-10-dihydroxytaxane of general formula 3a

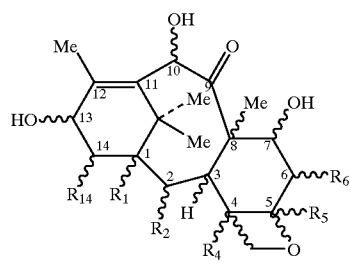

3a in which $R_1$, $R_2$, $R_4$, $R_5$, $R_6$ and $R_{14}$ are as defined above, in the presence of pyridine and/or of a hindered substituted pyridine.

2. The process according to claim 1, wherein $R_7$ represents an alkoxycarbonyl radical of general formula

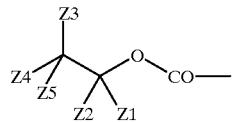

in which

Z1 and Z2 represent, independently of each other, a hydrogen atom, a radical R defined above or a halogen atom, Z3, Z4 and Z5 represent, independently of each other, a hydrogen atom, a halogen atom, a radical R, OR, $Si(R)_3$, R as defined above, or two of Z3, Z4 and Z5 together form part of a ring;

provided that when one of Z3, Z4 or Z5 represents a hydrogen atom, at least one of Z3, Z4 or Z5 represents a radical $Si(R)_3$, or two of Z3, Z4 and Z5 together form part of a ring; and provided that when one of Z3, Z4 or Z5 represents a halogen and Z1 and Z2 each represent a hydrogen atom, then Z3, Z4 and Z5 each represent a halogen selected from bromine and iodine.

3. The process according to claim 2, wherein Z1 and Z2 represent a hydrogen atom or an alkyl radical.

4. The process according to claim 2, wherein Z3, Z4 and Z5 each represent a bromine atom.

5. The process according to claim 2, wherein Z1 and Z2 each represent an alkyl radical, and Z3, Z4 and Z5 each represent a halogen atom.

6. The process according to claim 2, wherein two of Z3, Z4 and Z5 together form part of a fluorenyl ring.

7. The process according to claim 2, wherein the radical $R_7$ is selected from 2,2,2-tribromoethoxycarbonyl, 2-trichloromethyl-2-propoxycarbonyl, 2-trimethylsilylethoxycarbonyl and fluorenylmethoxycarbonyl groups.

8. The process according to claim 1, wherein the 10-hydroxytaxane of formula 3a is the 10-deacetylbaccatin of formula 2:

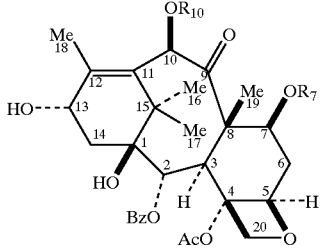

in which $R_{10}$ represents a hydrogen atom, and $R_7$ is defined above.

9. The process according to claim 1, wherein the esterification is carried out with 1 to 1.5 equivalents of an alkoxycarbonyl chloride substituted at the 2-position which is more hindered than 2,2,2-trichloroethoxycarbonyl in relation to the 7-10-dihydroxytaxane of general formula 3a.

10. The process according to claim 1, further comprising preparing a 7-(β-substituted-alkoxycarbonyloxy)-10-acyloxytaxane derivative of the following formula 3c:

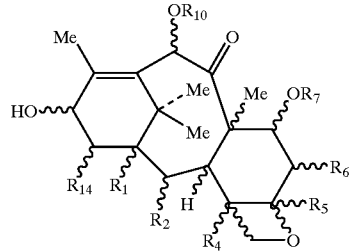

in which $R_1$, $R_2$, $R_4$, $R_5$, $R_6$, $R_7$ and $R_{14}$ are defined above, and $R_{10}$ represents an acyl radical of formula O—CO—R, R being defined above, wherein said process comprises the slow addition at room temperature of the acyl chloride, corresponding to the acyl radical at $R_{10}$ diluted in an appropriate solvent, to a vigorously stirred solution of the 7-(β-substituted-alkoxycarbonyloxy)-10-hydroxytaxane derivative of formula 3b defined above, in the presence of pyridine and/or of a hindered substituted pyridine.

11. The process according to claim 10, wherein R represents an alkyl group.

12. The process according to claim 1, wherein said appropriate solvent is a nonhydroxylated solvent.

13. The process according to claim 10, further comprising esterifying the hydroxyl at the 13-position of a taxane of formula 3c with an appropriate taxane side chain precursor, to obtain a taxane derivative of formula 3d:

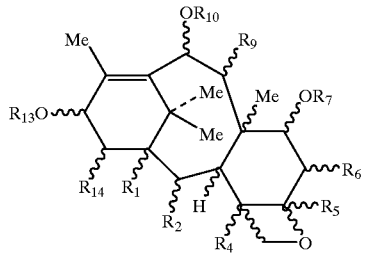

in which $R_1$, $R_2$, $R_4$, $R_5$, $R_6$, $R_7$, $R_{10}$ and $R_{14}$ are defined above, and $R_{13}$ represents a radical which is a taxane side chain precursor, followed by selective deprotection of the hydroxyl at the 7-position, optionally accompanied by and/or preceded by the opening and/or the conversion and/or the deprotection of the side chain precursor in order to obtain the desired taxane.

14. The process according to claim 13, wherein $R_{13}$ is the PACLITAXEL side chain precursor.

15. The process according to claim 13, wherein the deprotection of the hydroxyl at the 7-position is carried out by β-elimination.

16. A 7-(β-substituted-alkoxycarbonyloxy)-10-hydroxytaxane derivative corresponding to the formula 3b:

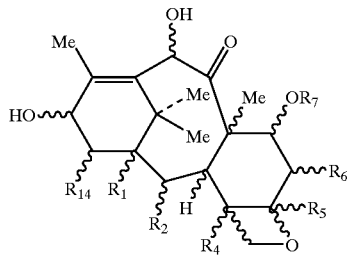

3b in which

R$_1$, R$_2$, R$_4$, R$_5$, R$_6$ and R$_{14}$ are each the same or different and each represents a radical Q, wherein:

Q is H, OH, R, OR, SH, SR, OCOR, OCOOR, HCO or X, wherein

X is a halogen atom, and

R represents a linear or branched alkyl, alkenyl or alkynyl radical, a perhaloalkyl radical, a linear or branched heteroalkyl, heteroalkenyl or heteroalkynyl radical, a cycloalkyl or cycloalkenyl radical, a heterocycloalkyl or heterocycloalkenyl radical, an aryl radical or an aralkyl radical, wherein said radicals are unsubstituted or substituted; and R$_7$ represents an alkoxycarbonyl group substituted at the 2-position which is more hindered than 2,2,2-trichloroethoxycarbonyl and which is removable by a β-elimination mechanism.

17. A derivative of the formula 3c:

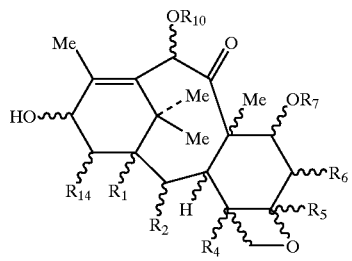

3c in which

R$_1$, R$_2$, R$_4$, R$_5$, R$_6$ and R$_{14}$ are each the same or different and each represents a radical Q, wherein:

Q is H, OH, R, OR, SH, SR, OCOR, OCOOR, HCO or X, wherein

X is a halogen atom, and

R represents a linear or branched alkyl, alkenyl or alkynyl radical, a perhaloalkyl radical, a linear or branched heteroalkyl, heteroalkenyl or heteroalkynyl radical, a cycloalkyl or cycloalkenyl radical, a heterocycloalkyl or heterocycloalkenyl radical, an aryl radical or an aralkyl radical, wherein said radicals are unsubstituted or substituted;

R$_7$ represents an alkoxycarbonyl group substituted at the 2-position which is more hindered than 2,2,2-trichloroethoxycarbonyl and which is removable by a β-elimination mechanism; and R$_{10}$ represents an acyl radical of formula O—CO—R, wherein R is defined above.

18. A derivative of the formula 3d:

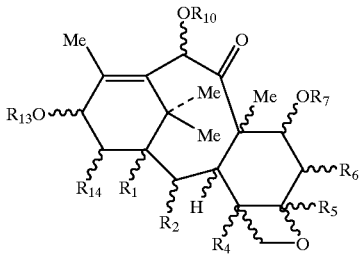

3d in which

R$_{13}$ represents a radical which is a taxane side chain precursor;

R$_1$, R$_2$, R$_4$, R$_5$, R$_6$, and R$_{14}$ are each the same or different and each represents a radical Q, wherein:

Q is H, OH, R, OR, SH, SR, OCOR, OCOOR, HCO or X, wherein

X is a halogen atom, and

R represents a linear or branched alkyl, alkenyl or alkynyl radical, a perhaloalkyl radical, a linear or branched heteroalkyl, heteroalkenyl or heteroalkynyl radical, a cycloalkyl or cycloalkenyl radical, a heterocycloalkyl or heterocycloalkenyl radical, an aryl radical or an aralkyl radical, wherein said radicals are unsubstituted or substituted;

R$_7$ represents an alkoxycarbonyl group substituted at the 2-position which is more hindered than 2,2,2-trichloroethoxycarbonyl and which is removable by a β-elimination mechanism; and R$_{10}$ represents an acyl radical of formula O—CO—R, wherein R is defined above.

19. The process according to claim 1, wherein said radicals are substituted with one or more halogen atoms.

20. The process according to claim 1, wherein said process is carried out at a temperature ranging from 20 to 80° C.

21. The process according to claim 1, wherein said hindered substituted pyridine is selected from 4-pyrolidinopyridine and dimethylaminopyridine.

22. The process according to claim 10, wherein said hindered substituted pyridine is selected from 4-pyrolidinopyridine and dimethylaminopyridine.

23. The process according to claim 11, wherein said alkyl group is methyl.

24. The process according to claim 12, wherein said nonhydroxylated solvent is an alkyl halide selected from methylene chloride, chloroform and dichloroethane.

* * * * *